(12) United States Patent
Seligman

(10) Patent No.: US 7,157,808 B2
(45) Date of Patent: Jan. 2, 2007

(54) POWER SUPPLY FOR A COCHLEAR IMPLANT

(75) Inventor: Peter Misha Seligman, Essendon (AU)

(73) Assignee: Cochlear Limited, Lane Cove (AU)

( * ) Notice: Subject to any disclaimer, the term of this patent is extended or adjusted under 35 U.S.C. 154(b) by 589 days.

(21) Appl. No.: 10/250,705

(22) PCT Filed: Jan. 24, 2002

(86) PCT No.: PCT/AU02/00074

§ 371 (c)(1),
(2), (4) Date: Jul. 7, 2003

(87) PCT Pub. No.: WO02/060029

PCT Pub. Date: Aug. 1, 2002

(65) Prior Publication Data

US 2004/0049243 A1    Mar. 11, 2004

(30) Foreign Application Priority Data

Jan. 24, 2001   (AU) .................................. PR2693

(51) Int. Cl.
*H20J 7/34* (2006.01)
(52) U.S. Cl. .................... 307/48; 607/57; 307/66; 307/130
(58) Field of Classification Search ............ 320/138; 307/48, 50, 54, 63, 71, 66, 130; 607/29, 607/34, 55, 56, 57
See application file for complete search history.

(56) References Cited

U.S. PATENT DOCUMENTS

| | | | |
|---|---|---|---|
| 3,930,192 A * | 12/1975 | Dinkler ...................... 320/119 |
| 4,081,738 A * | 3/1978 | Roller ........................ 320/117 |
| 4,315,162 A | 2/1982 | Ferguson | |
| 4,509,193 A | 4/1985 | Carlson | |
| 4,532,930 A | 8/1985 | Crosby et al. | |
| 4,563,621 A | 1/1986 | Moore | |
| 4,955,729 A | 9/1990 | Marx | |
| 5,355,071 A * | 10/1994 | Ishida et al. ................ 320/110 |
| 5,687,129 A | 11/1997 | Kim | |
| 5,696,833 A | 12/1997 | Matzen et al. | |
| 5,747,966 A | 5/1998 | Minamoto | |
| 5,876,425 A | 3/1999 | Gord et al. | |
| 5,956,241 A * | 9/1999 | LoCascio ................. 363/21.14 |
| 6,879,855 B1 * | 4/2005 | Schulman et al. ............. 607/2 |

FOREIGN PATENT DOCUMENTS

WO    WO 96/27932    9/1996

OTHER PUBLICATIONS

International Search Report of PCT/AU02/00074, dated Mar. 12, 2002.

(Continued)

*Primary Examiner*—Brian Sircus
*Assistant Examiner*—Andrew Deschere
(74) *Attorney, Agent, or Firm*—Christie, Parker & Hale, LLP.

(57) ABSTRACT

A power supply control system for use with a tissue stimulating prosthesis, such as a cochlear implant. The power supply control system comprises a first battery (31), a second battery (32), at least a third battery (33), and a switching system (36). The first and second batteries (31, 32) are electrically connected in series to provide power to the prosthesis, while the third battery (33) is electrically connectable through the switching means (36) in parallel with either the first battery (32). The third battery (33) is electrically connected by the control system in parallel with whichever one of said first battery (31) or said second battery (32) has lowest voltage.

31 Claims, 10 Drawing Sheets

OTHER PUBLICATIONS

International Preliminary Examination Report of PCT/AU02/00074, dated Sep. 18, 2002.

International Type Search Report for Australian Application No. PR 2693, dated Mar. 7, 2001.

* cited by examiner

POWER SUPPLY FOR A COCHLEAR IMPLANT

CROSS-REFERENCE TO RELATED APPLICATION

This application is a National Phase Patent Application of International Application Number PCT/AU02/00074, filed on Jan. 24, 2002, which claims priority of Australian Patent Application Number PR 2693, filed Jan. 24, 2001.

FIELD OF THE INVENTION

The present invention relates to a power supply for an implant, such as a cochlear implant, and in particular, to a power supply having a plurality of batteries and a means for controlling the use of the batteries by the implant.

BACKGROUND ART

In many people who are profoundly deaf, the reason for deafness is absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to, or an absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two essential components, an external component commonly referred to as a processor unit and an internal implanted component commonly referred to as a stimulator/receiver unit. Traditionally, both of these components have cooperated together to provide the sound sensation to a user.

The external component has traditionally consisted of a microphone for detecting sounds, such as speech and environmental sounds, a speech processor that converts the detected sounds into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil, which is positioned, to communicate with an implanted receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlea electrode which applies the electrical stimulation directly to the auditory nerve producing a hearing sensation corresponding to the original detected sound. As such, the implanted stimulator/receiver device has been a relatively passive unit that has relied on the reception of both power and data from the external unit to perform its required function.

Traditionally, the external componentry has been carried on the body of the user, such as in a pocket of the user's clothing, a belt pouch or in a harness, while the microphone has been mounted on a clip mounted behind the ear or on the lapel of the user.

More recently, due in the main to improvements in technology, the physical dimensions of the speech processor have been able to be reduced allowing for the external componentry to be housed in a small unit capable of being worn behind the ear of the user. This unit allows the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

The introduction of an external unit able to be positioned behind-the-ear (BTE) provides the user with increased freedom not previously experienced with the more conventional body worn external processor. A BTE unit does not require long cables connecting all of the components together and does not require a separate battery pack, but provides a single unit capable of being discretely worn behind the ear of a cochlear implant user which offers the same functionality of the body worn devices without the obvious restrictions that such devices place upon the user. Due to the obvious benefits such a device offers to the user, it is important that with increasing use of such a component that the reliability of the device be at least the equivalent of the previous body-worn devices. This is especially important with regard to the power supply incorporated in such a BTE device, as whilst it is much smaller, the power supply needs to be sufficient to ensure that the power demands of the implant are met, at least for an acceptable period of time.

As described above, battery cells are typically housed in the external componentry and provide the necessary power for the components of the implant.

In conventional body worn devices, other than BTE devices, the issue of ensuring that the power supply is sufficient to meet the needs of the implant is not of particular concern. This is due in the main to the fact that the size of the component is such that it can accommodate a substantial number of cells and a battery pack can be further employed with such a component. As this component is carried on the body in a harness or the like, the size of the component is not of great importance.

However, with the introduction and increased usage of BTE devices and the desire to provide such devices that are small enough to fit behind the ear of the user or to be discretely worn on the head of the user, the space requirements of the device lead to restrictions in the type and dimension of power supply that can be utilised. Where previously the number of cells required to form the power supply of the device has been relatively unrestricted, such more discrete and compact BTE devices have limited space to house the cells to be used to supply the power for the implant. Where a single battery cell provides insufficient power for all of the components, it has been known to mount two batteries in series within the external componentry.

One type of known battery cell used in cochlear implants and in implants utilising BTE units in particular such as those provided by the present applicant, is the zinc air cell.

Such cells have several practical advantages. They have a very high energy density and can supply a device's requirements for a relatively long period of time relative to their size and weight. They also have a relatively constant power output throughout most of their life, thereby reducing the risk of dangerous rapid discharge, such as shorting. Therefore, such cells have particular application to cochlear implants, which utilise these particular advantages. As supplied, these cells do, however, occasionally suffer from a relatively high failure rate. Testing undertaken by the present applicant suggests that approximately 8% of supplied zinc air cells do not perform satisfactorily on delivery. Given that some cochlear implants rely on two satisfactory cells being used in series, the chance that a user will have a problem after replacing a pair of such battery cells increases to 15%. Such problems include finding that the cochlear implant still does not work or stops working satisfactorily after a relatively short time following the insertion of new cells. These problems can then result in the user incorrectly believing that their device has failed and sending the device for repair or replacement, or finding themselves unexpectedly losing their ability to experience hearing sensation after they were sure that the power supply would last for a specific period of time.

When considering the amount of power that the external unit needs to supply to the implant, it should be appreciated that this can vary quite considerably from user to user. The amount of power required by the implant depends on a number of factors. The stimulation rate and speech processing strategy employed by the user dictates greatly the power requirements of the implant. If the implant needs to stimulate at high rates then more power will be required, as will also be the case if a complicated speech processing strategy is to be employed. Further to this, the power requirements are strongly influenced by the thickness of the skin separating the external and internal coils in the transcutaneous link. If this skin flap thickness is large, then the implant will require more power to transmit across such a medium than would be the case if the skin flap thickness is quite small.

In any regard it is important that the external unit is designed such that there is sufficient power available for a wide range of requirements, from those users with large skin flap thicknesses and high rate stimulation strategies to those with small skin flap thicknesses and lower rate strategies. This ensures that an off-the-shelf device can be supplied for all cases without the need for custom-made designs specific to the particular user's power requirements.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention provides a power supply for an electrically powered device, the power supply comprising a first plurality of batteries, a switching means, and a second plurality of batteries, wherein the first plurality of batteries are electrically connected in series and the second plurality of batteries are electrically connectable through the switching means in parallel with at least one of the first plurality of batteries.

According to a second aspect, the present invention provides a power supply for an electrically powered device, the power supply comprising a first battery, a second battery, at least a third battery, and a switching means, the first and second battery being electrically connected in series and the at least third battery being electrically connectable through the switching means in parallel with either the first battery or the second battery.

In a preferred embodiment, the third battery is connected in parallel by the switching means with whichever of the first and second batteries is exhibiting worse performance, which could be determined by which battery has the lower voltage. In this embodiment, the batteries will tend to work at substantially the same voltage and thus substantially evenly share the power load of the electrically powered device. Such an arrangement has the advantage that the probability of failure of a power supply having three batteries in such an arrangement reduces to 2% and so the probability of a successful battery change increases to 98%, based on batteries having an 8% probability of being faulty.

The switching means preferably comprises an analog changeover switch, operable to connect the third battery in parallel with the first battery or the second battery, and which may also be operable to disconnect the third battery from both the first and second batteries. A low power comparator can be used to compare the mid-point from a voltage divider. When the mid-point of the batteries indicates a mismatch, the power supply preferably operates the switch to connect the third battery in parallel with whichever of the first or second batteries has the lowest voltage. A small amount of hysteresis (eg. about 4 mV) can be provided to avoid excessive switching. The switching rate is preferably limited to below about 50 kHz, more preferably, of the order of 20 kHz.

In the above embodiment, because all of the batteries are operating at substantially the same voltage (preferably within 8 mV), two of the batteries are effectively in parallel. As switching between the batteries occurs, only relatively small surge currents are preferably generated.

In one embodiment, the batteries of the power supply can be rechargeable.

According to a third aspect, the present invention provides a power supply control system for use with a tissue stimulating prosthesis, the power supply control system comprising a first plurality of batteries, a switching means and a second plurality of batteries, the first plurality of batteries being electrically connected in series to provide power to the prosthesis, and at least one of the second plurality of batteries being electrically connectable through the switching means in parallel with at least one of the first plurality of batteries; wherein the at least one of the second plurality of batteries is electrically connected by the control system in parallel with whichever one of said first plurality of batteries has the lowest voltage.

According to a fourth aspect, the present invention is a power supply control system for use with a tissue stimulating prosthesis, the power supply control system comprising a first battery, a second battery, at least a third battery, and a switching means, the first and second battery being electrically connected in series to provide power to the prosthesis, and the at least third battery being electrically connectable through the switching means in parallel with either the first battery or the second battery; wherein the at least third battery is electrically connected by the control system in parallel with whichever one of said first battery or said second battery has the lowest voltage.

According to a fifth aspect, the present invention provides a power supply control system for use with a tissue stimulating prosthesis, the power supply control system comprising a first plurality of batteries, a second plurality of batteries, and a switching means, the first plurality of batteries being electrically connected in series to provide power to the prosthesis, and at least one of the second plurality of batteries being electrically connectable through the switching means in parallel with at least one of the first plurality of batteries; wherein the at least one of the second plurality of batteries is electrically connected by the control system in parallel with one of said first plurality of batteries following detection by the control system that the voltage of said one of said first plurality of batteries is below a predetermined threshold.

The predetermined threshold may be determined by reference to a voltage of another of the first plurality of batteries.

According to a sixth aspect, the present invention provides a power supply control system for use with a tissue stimulating prosthesis, the power supply control system comprising a first battery, a second battery, at least a third battery, and a switching means, the first and second battery being electrically connected in series to provide power to the prosthesis, and the at least third battery being electrically connectable through the switching means in parallel with either the first battery or the second battery; wherein the at least third battery is electrically connected by the control system in parallel with one of said first battery or said second battery following detection by the control system that the voltage of said first battery or said second battery is below a predetermined threshold.

According to a seventh aspect, the present invention provides a power supply control system for use with a tissue stimulating prosthesis, the power supply control system comprising:

a first battery;

a second battery connected in series with the first battery to provide power to the prosthesis; and a third battery being electrically connectable via switching means in parallel with either the first battery or the second battery; wherein the control system controls the switching means to electrically connect the third battery in parallel with said first battery or said second battery based on a determination by the control system that the operation of said first battery or said second battery is below a predetermined threshold.

In these aspects, the batteries will tend to work at substantially the same voltage and thus share the power load of the prosthesis. Such an arrangement has the advantage that the probability of failure of a power supply having three batteries reduces to 2% and so the probability of a successful battery change increases to 98%. Such an arrangement also ensures that should the system power requirements be too great for the two batteries in series alone, the third battery will be electrically connected to cover any increased power requirements.

The switching means of the present invention preferably comprises an analog changeover switch. In preferred embodiments of the seventh aspect of the present invention, a low power comparator may be used to make the determination of satisfactory operation of the first and second batteries, for example by being used to compare the mid-point from a voltage divider positioned across the first and second batteries. Such a comparator may also be used in voltage measurements of the batteries in accordance with the first to sixth aspects of the present invention. In such embodiments, when the mid-point of the batteries indicates a mismatch, the comparator preferably operates the switch to connect the third battery in parallel with whichever of the first or second batteries has the lowest voltage. As the third battery will approximately halve the demand on the battery with which it is connected in parallel, the other of the first and second batteries will be drained at a faster rate. Hence, it is expected that it will repeatedly be necessary to connect the third battery across the other of the first and second batteries. The control system preferably causes such switching of the third battery between the first and second batteries to occur based on the voltages measured by the voltage divider. In this regard, a small amount of hysteresis (eg. about 4 mV) is preferably provided to avoid excessive switching. The switching rate is preferably limited to below about 50 kHz. Such regular switching of the third battery between the first and second batteries will assist in ensuring the first and second batteries are drained at a similar rate.

In one embodiment, the tissue-stimulating prosthesis can comprise a cochlear implant. The cochlear implant can comprise an externally mounted device that includes a speech processor.

For the purposes of the description provided below, reference will be made to the prosthesis in the form of a cochlear implant. It is to be appreciated that the following description could apply, with appropriate modification, to other systems adapted for implantation into body tissue.

When in use, the power supply control system preferably controls the power supply for the microphone, speech processor, electrode array and any other electrical or electronic componentry of the cochlear implant system. The power supply control system preferably ensures that not only is the power load shared with all of the batteries of the system but also that should the system power requirements be large, such as in cases of large skin flap thickness and high stimulation rate, then the power supply is able to meet such needs.

In one embodiment, the power supply can be mounted within a case that also encloses the componentry of the electrical equipment, such as the processor means of the cochlear implant. In another embodiment, the power supply can be mounted within a separate case with electrical connection provided between the batteries and the componentry, such as the processor means.

The first, second, and at least the third battery can each comprise a zinc-air cell. It will, however, be appreciated that any suitable battery cell could be utilised in the present invention. Each of the batteries are also preferably surrounded by an electrically insulating material such that the batteries are electrically insulated from the case in which they are mounted.

A battery charging means can be used to recharge the batteries of the power supply.

In accordance with an eighth aspect, the present invention provides a method of operating a power supply, the method comprising the steps of electrically connecting a first battery and a second battery in series; and electrically connecting a third battery in parallel with whichever battery of the first battery and the second battery exhibits worse performance.

In accordance with a ninth aspect, the present invention provides a method of operating a power supply for a tissue-stimulating prosthesis, the method comprising the steps of electrically connecting a first battery and a second battery in series; and electrically connecting a third battery in parallel with whichever battery of the first battery and the second battery exhibits worse performance.

The methods of the eighth and ninth aspects of the invention preferably further comprise the step of measuring the performance of the first battery and the second battery.

The methods of the eighth and ninth aspects of the invention preferably further comprise, prior to the step of measuring the performance of the first battery and the second battery, disconnecting the third battery from a parallel connection with either of the first battery or the second battery.

Such a step ensures that the measurement of performance of the first battery and the second battery, such as by measuring the voltage across each of the first and second batteries, is carried out without the performance of the third battery affecting the measurement.

Preferred embodiments of the present invention provide a system designed to maximise the performance of devices such as cochlear implants and other devices that are reliant upon installed battery power, in the presence of an unreliable power supply. Preferred embodiments of the invention may also provide a system designed to cater for the power requirements of a wide range of cochlear implant or tissue-stimulating implant users with varying system requirements.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
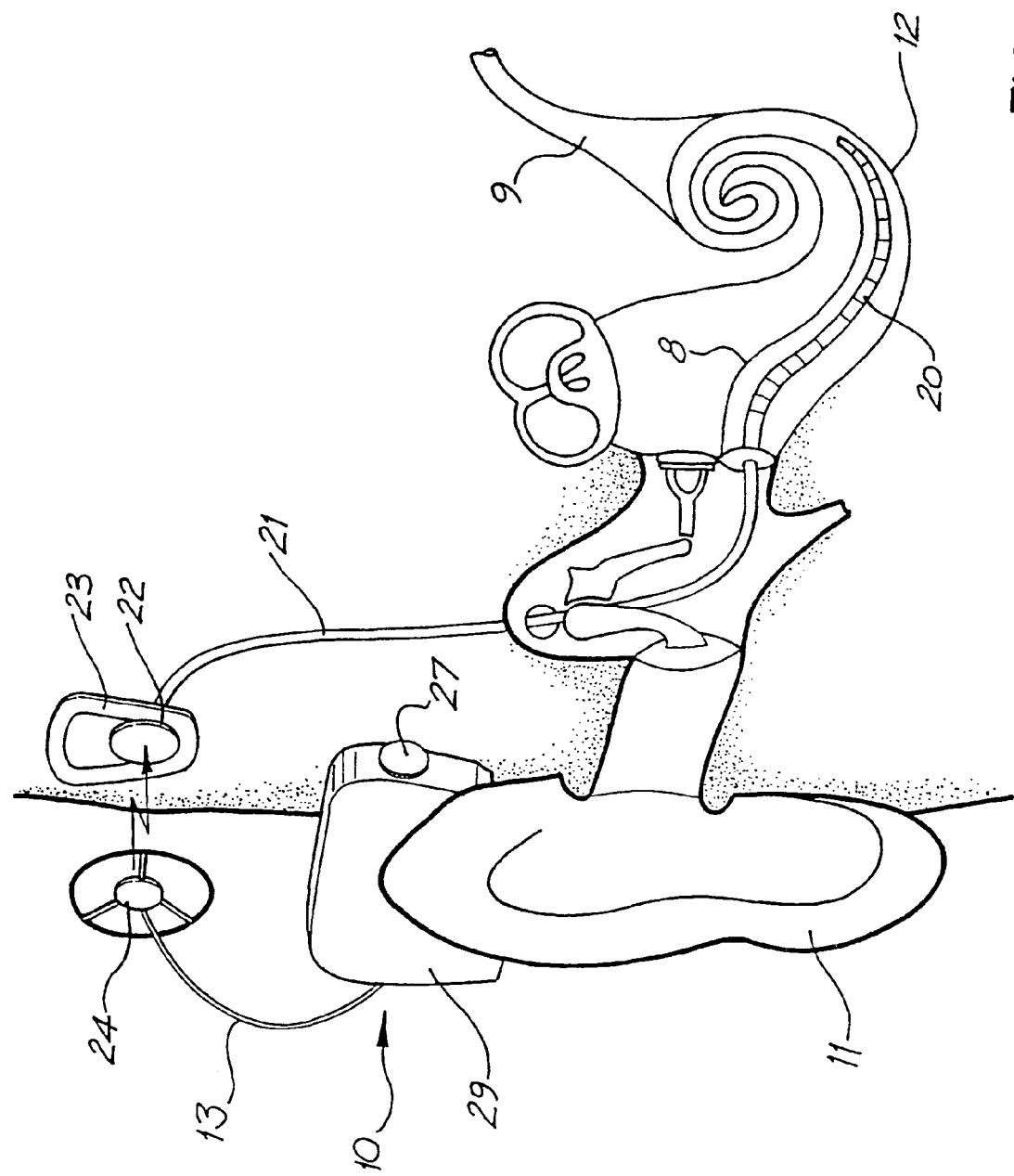
FIG. 1 is a pictorial representation of a typical cochlear implant system incorporating the present invention.

An example of a device powered by the power supply system of the present invention can be seen in FIG. 1.

One embodiment of a cochlear implant utilising the present invention is depicted in FIG. 1 and consists of two main components, namely an external component 10 including a speech processor 29, and an internal component including an implanted receiver and stimulator unit 22.

The external component 10 includes an on-board microphone 27. The case of the external component 10 is constructed and arranged so that it can sit on the outer ear 11 of the implantee. The case of the external component is also constructed so that it contains a power supply in accordance with the present invention. The power supply provides the power for the entire implant system.

A cable 13 extends from the case of the external component 10 to an external transmitter coil 24 which transmits electrical signals to the implanted unit 22 via a radio frequency (RF) Link.

The implanted component includes a receiver coil 23 for receiving power and data transmitted from the transmitter coil 24. A cable 21 also extends from the implanted receiver and stimulator unit 22 to the cochlear 12 and terminates in an electrode array 20. The signals thus received are applied by the array 20 to the basilar membrane 8 thereby stimulating an auditory nerve 9. The operation of such a device is described, for example, in U.S. Pat. No. 4,532,930.

Such a cochlear implant system as described in FIG. 1 requires a power supply capable of being incorporated in the relatively small case of the external component 10 so that it can be positioned behind the ear of the implant user. Further, the voltage of the power supply of this system also needs to be sufficient to provide a reliable supply of power to the system even in cases where the user has a large skin flap thickness between transmitter coil 24 and receiver coil 23 resulting in increased power requirements to transmit the applicable data/power to the implanted unit 22. The present invention provides a reliable solution to these requirements.

Figure 2:
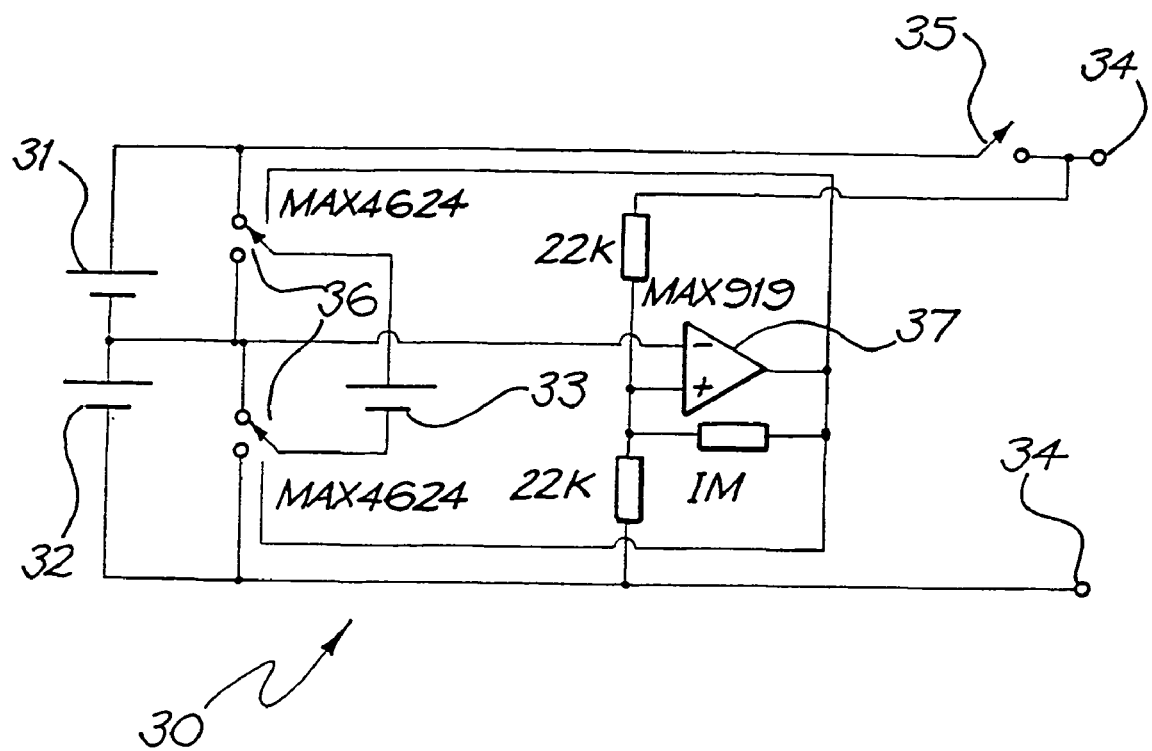
FIG. 2 is a circuit layout of a power supply for use in electrically powering a cochlear implant.

One example of a circuit layout for a power supply that is housed in the case of the external component 10 for powering a cochlear implant is depicted generally as 30 in FIG. 2.

The power supply circuit 30 includes first battery 31 and a second battery 32 electrically connected in series. The output of the power supply is provided at terminals 34 and can be switched on or off using the On/Off switch 35.

The power supply circuit 30 further includes at least a third battery 33 that is electrically connectable in parallel with either the first battery 31 or the second battery 32 through an analog changeover switch 36.

In the depicted embodiment, the third battery 33 is connected in parallel by switch 36 with whichever of the first and second batteries 31,32 has the lowest voltage. In this embodiment, the batteries 31,32,33 all tend to work at substantially the same voltage and thus substantially evenly share the power load of the cochlear implant powered by the power supply circuit 30.

Such an arrangement has the advantage that the probability of failure of a power supply having three batteries in such an arrangement reduces to 2% and so the probability of a successful battery change increases to 98%, based on batteries having an 8% probability of being faulty at the time of supply as tests by the applicant have revealed.

In the depicted embodiment, a comparator 37 is used to compare the mid-point from a voltage divider. When the mid-point of the first and second batteries 31,32 indicates a mismatch, the comparator 37 operates the switch 36 to connect the third battery 33 in parallel with whichever of the first or second batteries 31,32 has the lowest voltage. A small amount of hysteresis (eg. about 4 mV) is built into the comparator to avoid excessive switching of switch 36. In the depicted embodiment, the switching rate is of the order of about 20 kHz.

In the above embodiment, because all of the batteries 31, 32, 33 are operating at the same voltage (within 8 mV), the batteries are effectively in parallel. As switching between the batteries occurs, only relatively small surge currents are generated since the small voltage difference (8 mV) across the internal resistance (perhaps 20 ohms) amounts to only around 0.4 mA.

A prototype of the circuit shown in FIG. 2 has been tested, and displayed efficiency extremely close to 100%. The estimated losses at full load of the circuit include a 400 μW series loss in the switch "on" resistances, a 13 μW switching loss in the comparator, a 13 μW loss due to driving of switch capacitances, and a 15 μW resistive loss in the voltage divider. Peak efficiency occurs at an output power of 15 mW giving 99.5% efficiency, while efficiency of 99% is displayed at 2.5 mW and 44 mW output power. Ripple and noise levels were acceptable.

Figure 3:
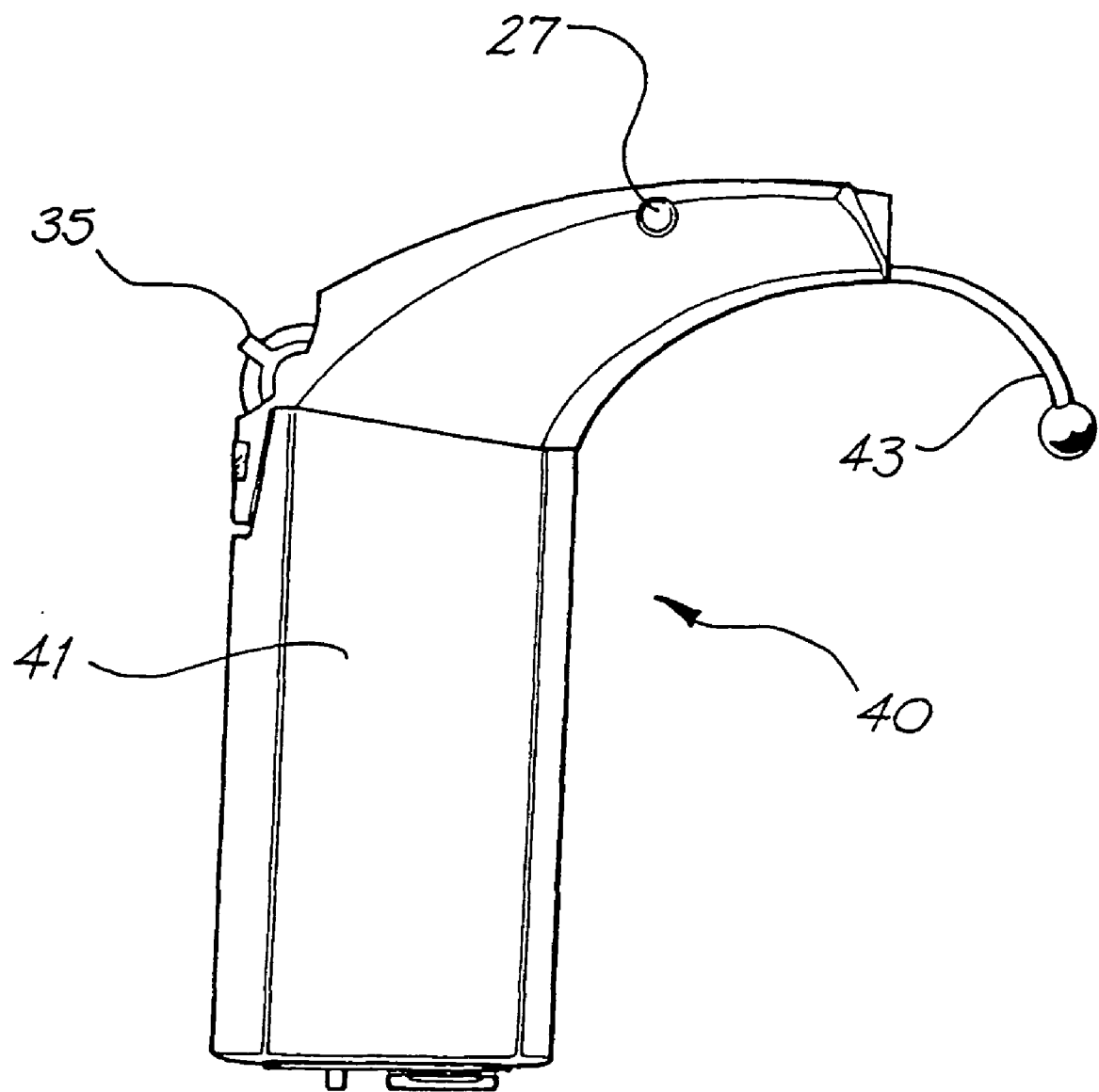
FIG. 3 is a side elevational view of another embodiment of the external component of a cochlear implant having the power supply control system of the present invention.

As described above, one example of a device that can be powered by the power supply 30 is a tissue-stimulating cochlear implant prosthesis that has components adapted for implant in an implantee's body. Another embodiment of an external component for such an implant is depicted as 40 in FIGS. 3 and 4. The external component 40 houses a speech processor, and, has an in-built microphone 27.

Figure 4:
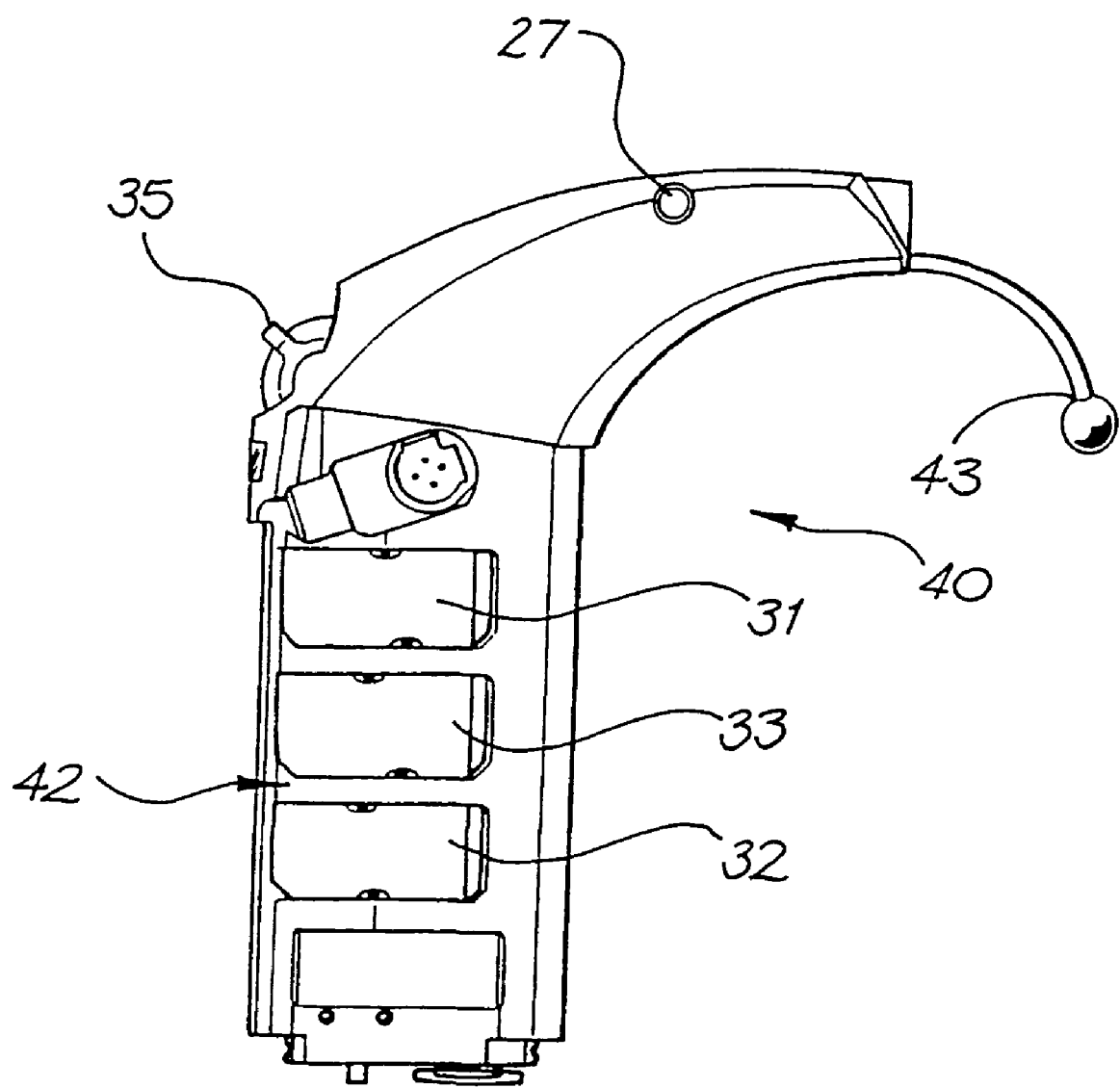
FIG. 4 is a side elevational view of the external component of the cochlear implant of FIG. 3 with the battery compartment cover removed.

The component 40 has a removable cover 41 enclosing a battery compartment 42. FIG. 4 depicts the component 40 with the cover 41 removed. Housed within compartment 42 are the first and second batteries 31,32 connected in series, and third battery 33.

When in use, the batteries 31, 32, 33 provide power for all components of the cochlear implant including the microphone 27, a speech processor, the implanted electrode array, and any other electrical or electronic componentry of the cochlear implant whether it be external or internal of the body of the implantee.

While the batteries can be mounted within the case that also encloses the other componentry of the external component 40, the batteries could be mounted within a separate case with electrical connection provided between the batteries and the componentry of the implant, such as the speech processor.

The depicted batteries 31,32,33 each comprise a zinc-air cell. It will, however, be appreciated that any suitable battery cell could be utilised in the present invention. When mounted in a prosthesis, each of the batteries 31,32,33 are also preferably surrounded by an electrically insulating material such that the batteries are electrically insulated from the case in which they are mounted.

The batteries are preferably all of the same design, however the present invention may be applied to batteries having some differences in design. The present invention may also be applied to the use of rechargeable batteries.

Figure 5:
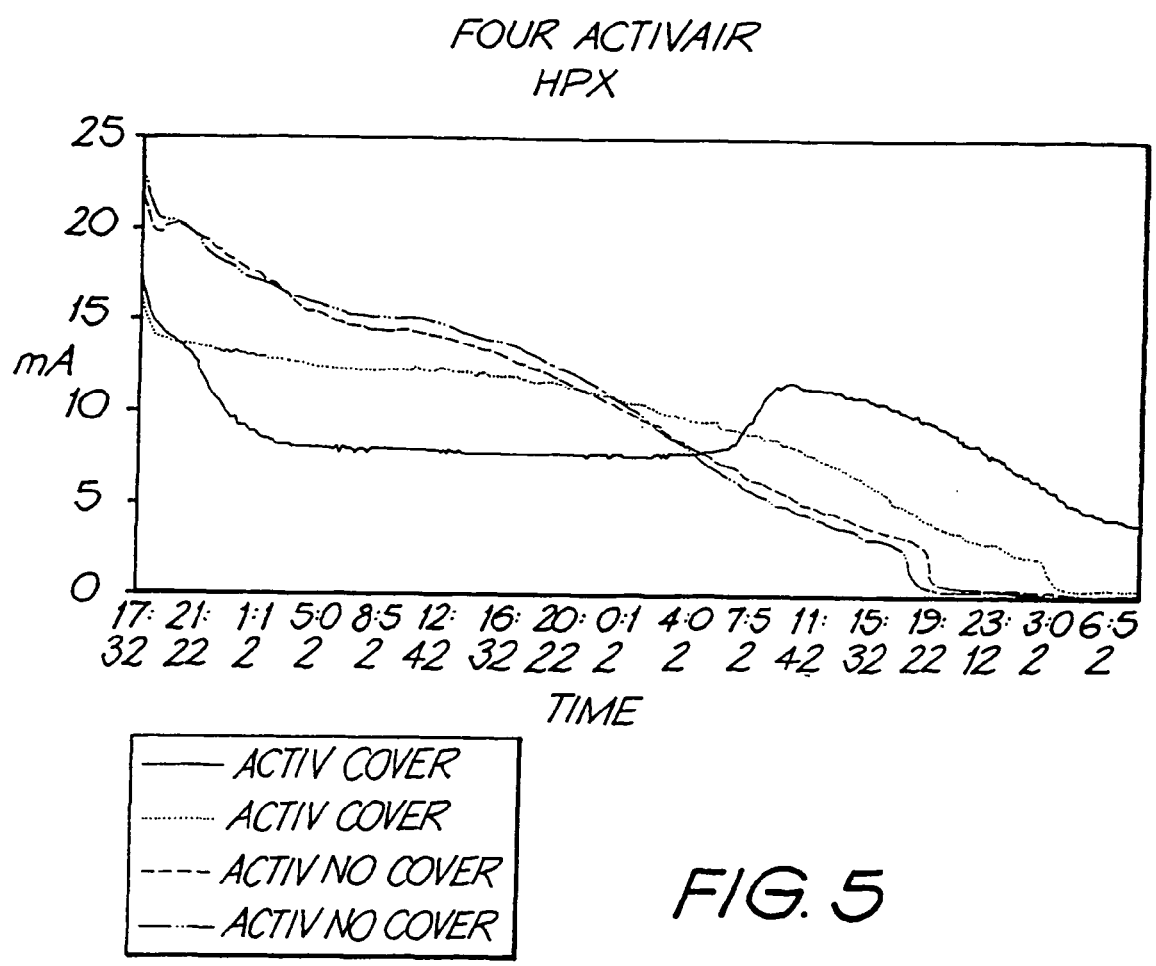
FIGS. 5 to 7 illustrate typical limiting currents of various cells.
Figure 6:
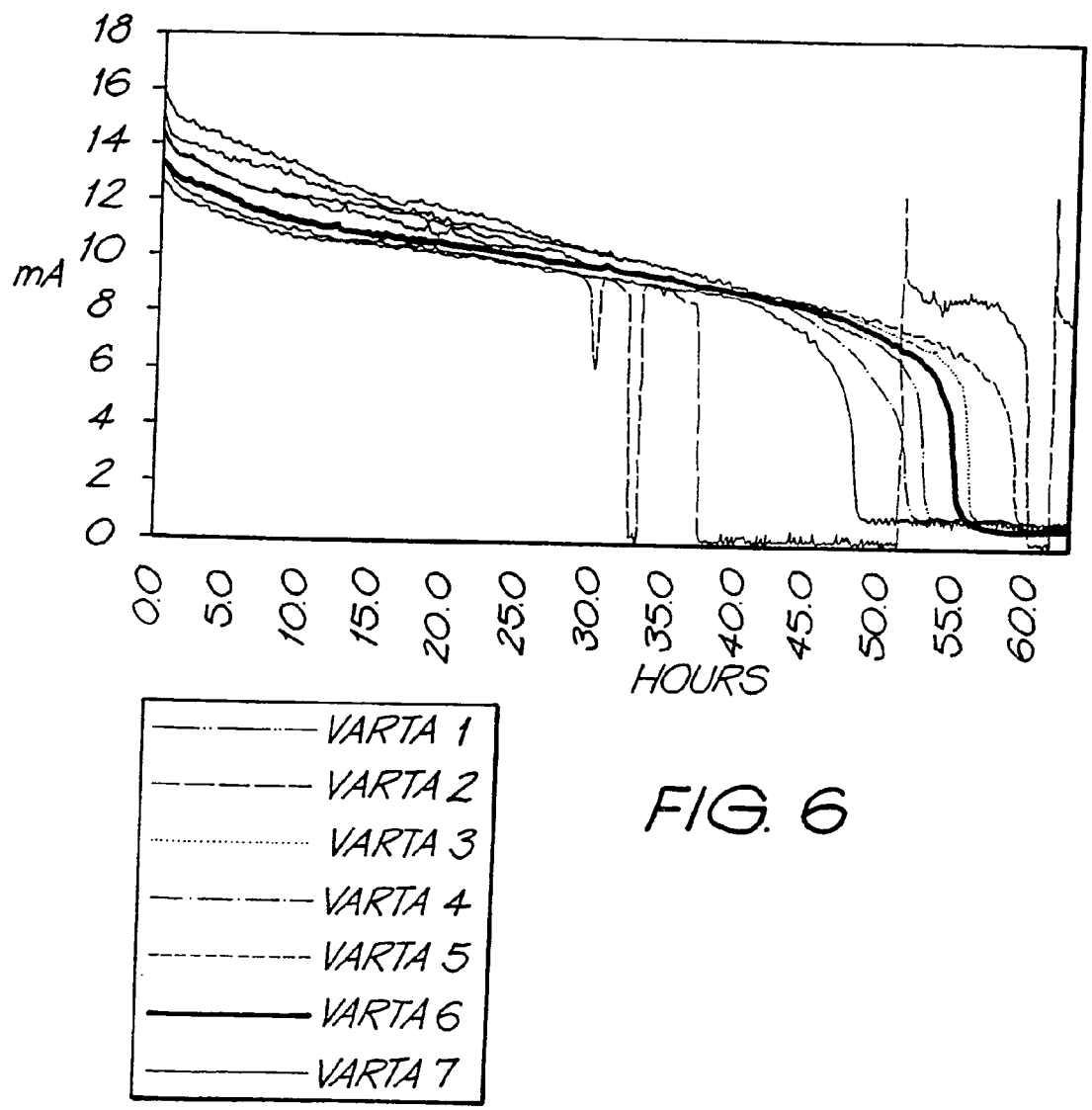
Figure 7:
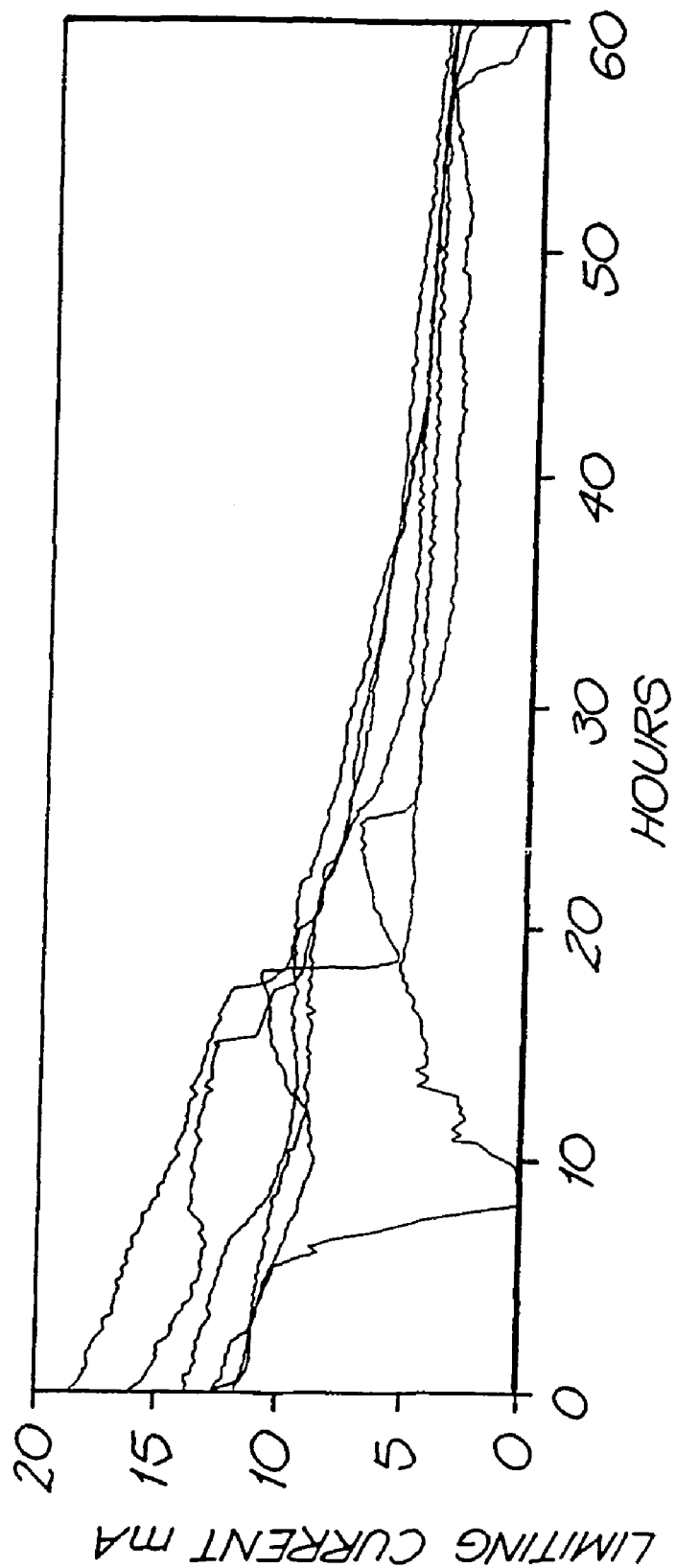

FIG. 5 illustrates typical limiting currents of each of four 675 size zinc-air Activair HPX battery cells, presented as limiting current in mA vs time. FIG. 6 illustrates typical limiting currents of each of seven 675 size zinc-air Varta V675 battery cells, again presented as limiting current in mA vs time. FIG. 7 illustrates the performance of six pairs of Rayovac 675 size zinc-air cells, presented as limiting current in mA vs time. As can be seen from FIGS. 5–7, the reliability of such cells is relatively poor, with the performance from one cell to the next being relatively inconsistent.

Figure 8:
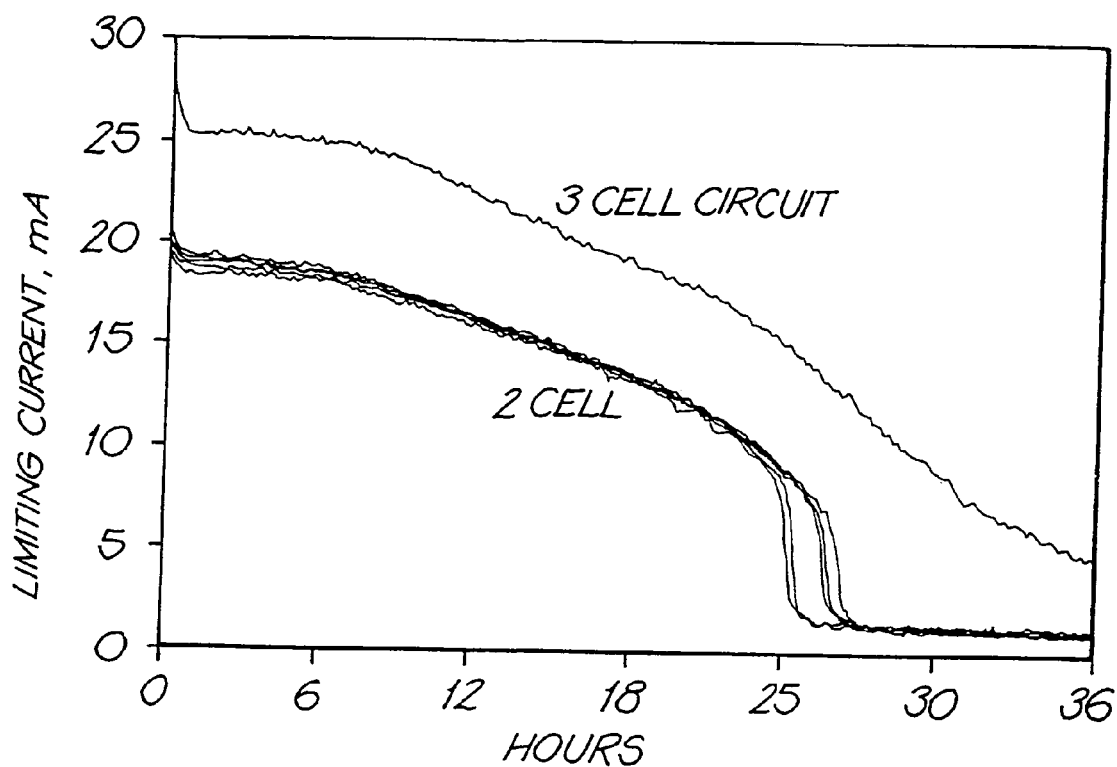
FIG. 8 illustrates the limiting current over time exhibited by a 3 cell embodiment of the present invention and by a prior art 2 cell arrangement, when loaded by a constant 2.2 Volt load.
Figure 9:
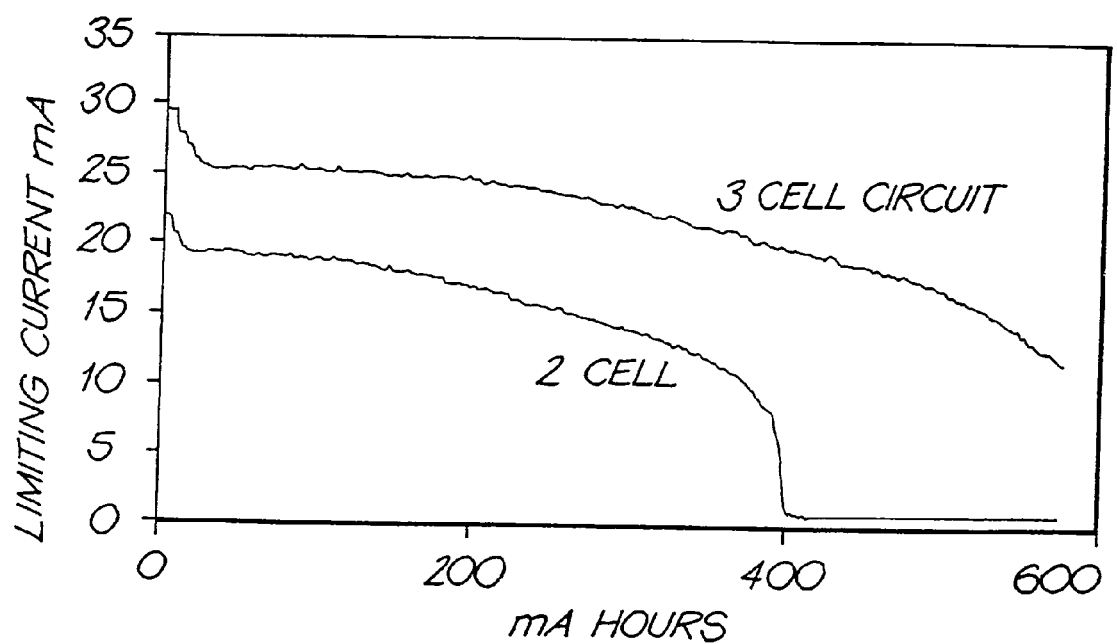
FIG. 9 illustrates the limiting current vs mA hours for the 3 cell embodiment of the present invention and the 2 cell prior art arrangement referred to in FIG. 8.

FIG. 8 illustrates the limiting current over time exhibited by a 3 cell embodiment of the present invention compared with the limiting current over time of three prior art 2 cell arrangements, when loaded by a constant 2.2 Volt load. As can be seen, the 3 cell arrangement of the present invention significantly improves the limiting current of the power supply, such that any given load current can be supplied for a longer time by the present embodiment of the invention than the prior art two cell arrangement. This is better shown in FIG. 9, which illustrates the limiting current vs mA hours for the 3 cell embodiment of the present invention and the 2 cell prior art arrangement. As can be seen, for a load current of, say, 15 mA, the available capacity has increased from 268 mA hours to 536 mA hours, exactly double. Discharging the cells to exhaustion revealed a capacity increase from 350 mAh for the prior art 2 cell arrangement to 572 mAh for the present embodiment of the invention. Hence, the present embodiment of the invention exhibits a 63% greater capacity than the 2 cell prior art arrangement, which is a better improvement than the 50% expected improvement. This may be due to a increased capacity of the batteries when loaded less heavily.

Figure 10:
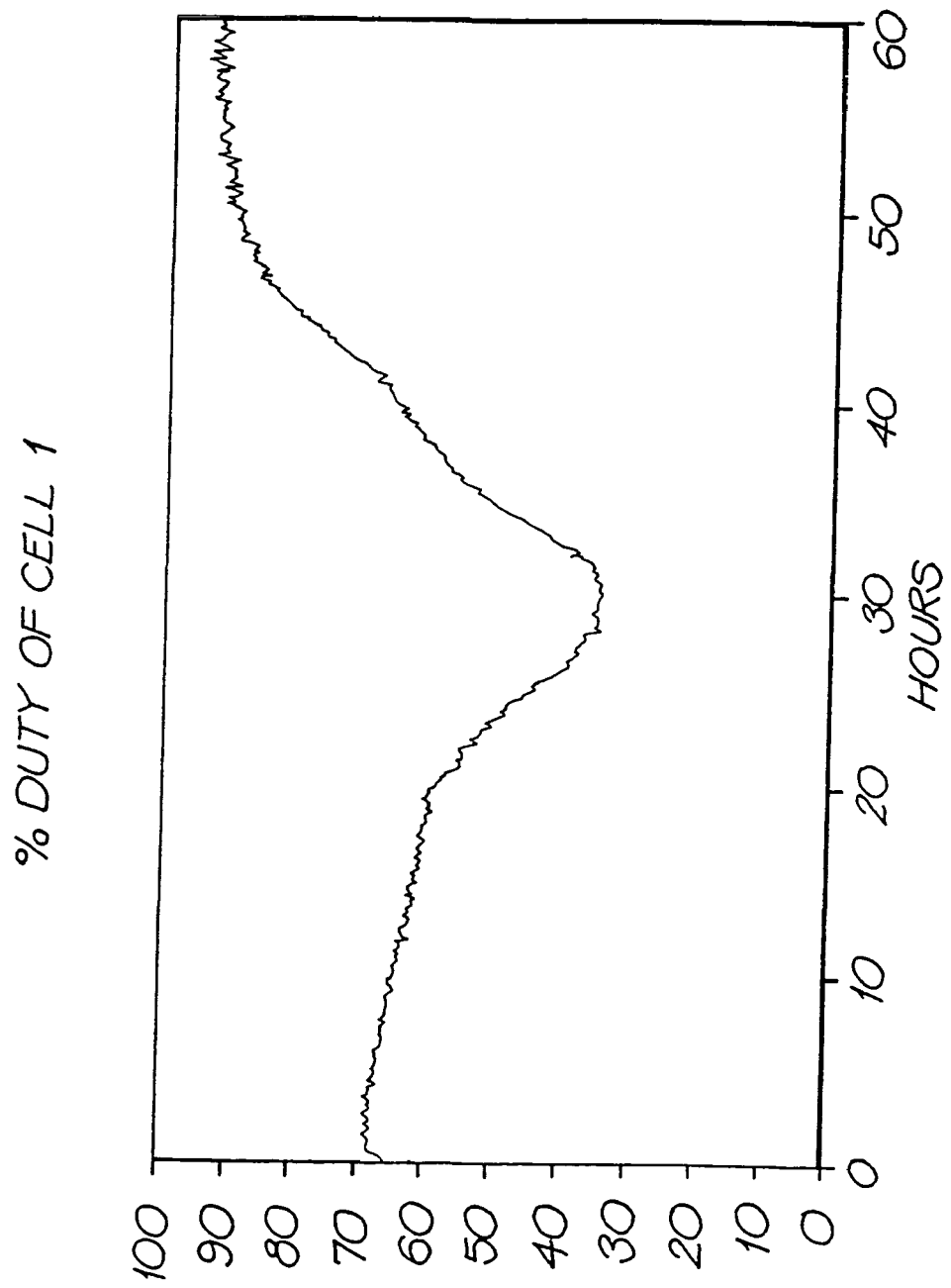
FIG. 10 illustrates the duty cycle of a battery of the present embodiment of the invention.

Finally, to demonstrate the action of the third battery cell, the percentage of time that one of the two series cells was connected in parallel with the third cell was recorded over time. The results are displayed in FIG. 10. FIG. 10 shows that, initially, the first of the series cells carried more current for much of the time than the second. However, from 24 hours to 35 hours the situation was reversed and the other cell carried more current. This demonstrates the ability of the system to adapt to the randomly varying output of the cells and imbalances between the cells.

While the illustrated and described embodiment comprises two batteries placed in series and a third battery being electrically connectable through a switching means in parallel with either of the two batteries placed in series, it is envisaged that more than three batteries could be used, employing more than two batteries in series and more than one battery electrically connectable in parallel with one or more of the series-connected batteries without going beyond the scope of the present invention.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A power supply for an electrically powered device comprising:
   a first battery;
   a second battery;
   at least a third battery; and
   a switching means;
   wherein, the first and second battery being electrically connected in series, and the at least a third battery being electrically connected by the switching means in parallel with one of the first battery or the second battery which has a lower voltage,
   when the lower voltage is below the voltage of the other one of the first and second batteries by a predetermined value.

2. The power supply of claim 1 wherein the switching means comprises an analog changeover switch.

3. The power supply of claim 1 further comprising a comparator that compares a mid-point voltage from a voltage divider with the predetermined value, such that when a mid-point voltage of the batteries indicates a mismatch with the predetermined value, the power supply operates the switching means to connect the third battery in parallel with the one of the first or second batteries which has the lower voltage.

4. The power supply of claim 3 wherein the comparator is a low power comparator.

5. The power supply of claim 1 wherein the predetermined value is at least 4 mV.

6. The power supply of claim 1 wherein at least one of the batteries of the power supply is rechargeable.

7. A power supply control system for use with a tissue stimulating prosthesis comprising:
- a first battery;
- a second battery;
- at least a third battery; and
- a switching means
- wherein, the first and second battery being electrically connected in series to provide power to the prosthesis, and the at least a third battery being electrically connected by the switching means in parallel with one of the first battery or the second battery which has a lower voltage,
- when the lower voltage is below the voltage of the other one of the first and second batteries by a predetermined value.

8. The power supply control system of claim 7 wherein the switching means comprises an analog changeover switch.

9. The power supply control system of claim 7 further comprising a comparator that compares a mid-point voltage from a voltage divider positioned across the first and second batteries with the predetermined value, such that when a mid-point voltage of the batteries indicates a mismatch, the power supply control system operates the switching means to connect the third battery in parallel with the one of the first or second batteries which has the lower voltage.

10. The power supply control system of claim 7, wherein the predetermined value is at least 4 mV.

11. The power supply control system of claim 7 wherein the tissue-stimulating prosthesis comprises a cochlear implant.

12. The power supply control system of claim 11 wherein the cochlear implant comprises an external component that houses a speech processor.

13. The power supply control system of claim 12 wherein the external component has a case, the power supply being mounted within the case.

14. The power supply control system of claim 7 wherein the first, second, and at least the third battery each comprise a zinc-air cell.

15. A power supply control system for use with a tissue stimulating prosthesis comprising:
- a first battery;
- a second battery;
- at least a third battery; and
- a switching means
- wherein, the first and second battery being electrically connected in series to provide power to the prosthesis, and the at least a third battery being electrically connected by the switching means in parallel with either one of the first battery or the second battery which has a lower voltage,
- when the lower voltage is below the voltage of the other one of the first and second batteries by a predetermined value.

16. The power supply control system of claim 15 wherein the switching means comprises an analog changeover switch.

17. The power supply control system of claim 15 further comprising a comparator that compares a mid-point voltage from a voltage divider positioned across the first and second batteries with the predetermined value, such that when a mid-point voltage of the batteries indicates a mismatch, the power supply control system operates the switching means to connect the third battery in parallel with the one of the first or second batteries which has the lower voltage.

18. The power supply control system of claim 15 wherein the predetermined value 4 mV.

19. The power supply control system of claim 15 wherein the tissue-stimulating prosthesis comprises a cochlear implant.

20. The power supply control system of claim 19 wherein the cochlear implant comprises an external component that houses a speech processor.

21. The power supply control system of claim 20 wherein the external component has a case, the power supply being mounted within the case.

22. The power supply control system of claim 15 wherein the first, second, and at least the third battery each comprise a zinc-air cell.

23. A power supply control system for use with a tissue stimulating prosthesis, the power supply control system comprising:
- a first battery;
- a second battery connected in series with the first battery to provide power to the prosthesis; and
- a third battery being electrically in parallel with one of the first battery or the second battery by a switching means;
- wherein the control system controls the switching means to electrically connect the third battery in parallel with said one of the first battery or the second battery based on a determination by the control system that the operation of said first battery or said second battery is below a predetermined voltage value and
- wherein the switching means operates only when the voltage of the battery of the first and second batteries having a lower voltage is below the voltage of the other battery of the first and second batteries by the predetermined voltage value.

24. The power supply control system of claim 23 wherein the control system is operable to measure a voltage of the first battery and a voltage of the second battery in order to make the determination of which of said first battery and said second battery are below the predetermined voltage value.

25. The power supply control system of claim 23 wherein the switching means comprises an analog changeover switch.

26. The power supply control system of claim 23 further comprising a comparator that compares a mid-point voltage from a voltage divider positioned across the first and second batteries with the predetermined voltage value, such that when a mid-point voltage of the batteries indicates a mismatch, the power supply control system operates the switching means to connect the third battery in parallel with the one of the first or second batteries which has the lower voltage.

27. The power supply control system of claim 23 wherein the predetermined voltage is at least 4 mV.

28. The power supply control system of claim 23 wherein the tissue-stimulating prosthesis comprises a cochlear implant.

29. The power supply control system of claim 28 wherein the cochlear implant comprises an external component that houses a speech processor.

30. The power supply control system of claim 29 wherein the external component has a case, the power supply being mounted within the case.

31. The power supply control system of claim 23 wherein the first, second, and at least the third battery each comprise a zinc-air cell.

* * * * *

UNITED STATES PATENT AND TRADEMARK OFFICE
CERTIFICATE OF CORRECTION

PATENT NO. : 7,157,808 B2
APPLICATION NO. : 10/250705
DATED : January 2, 2007
INVENTOR(S) : Seligman It is certified that error appears in the above-identified patent and that said Letters Patent is hereby corrected as shown below:

On the Title Page

Item (57) Abstract, line 9    Delete "either the first battery (32.)",
Insert --either the first battery (31) or the second battery (32).--

In the Claims

Column 11, line 52, Claim 15    Delete "either"

Column 12, line 2, Claim 18    After "predetermined value",
Insert --is at least--

Column 12, line 38, Claim 24    Delete "are",
Insert --is--

Column 12, line 53, Claim 27    After "voltage",
Insert --value--

Signed and Sealed this

Seventh Day of August, 2007

JON W. DUDAS
*Director of the United States Patent and Trademark Office*